US011125671B2

(12) United States Patent
Santagati et al.

(10) Patent No.: US 11,125,671 B2
(45) Date of Patent: Sep. 21, 2021

(54) LABORATORY MEASUREMENT OF DYNAMIC FRACTURE POROSITY AND PERMEABILITY VARIATIONS IN ROCK CORE PLUG SAMPLES

(71) Applicant: Saudi Arabian Oil Company, Dhahran (SA)

(72) Inventors: Antonio A Santagati, Dhahran (SA); Otto E. Meza Camargo, Dhahran (SA); Tariq Mahmood, Dhahran (SA); Edwin Caliboso, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 233 days.

(21) Appl. No.: 16/506,689

(22) Filed: Jul. 9, 2019

(65) Prior Publication Data

US 2021/0010922 A1 Jan. 14, 2021

(51) Int. Cl.
*G01N 15/08* (2006.01)
*G01N 33/24* (2006.01)

(52) U.S. Cl.
CPC ....... *G01N 15/0826* (2013.01); *G01N 33/241* (2013.01); *G01N 15/088* (2013.01)

(58) Field of Classification Search
CPC ............ G01N 15/0826; G01N 15/088; G01N 2015/0846; G01N 2223/616; G01N 33/241
See application file for complete search history.

(56) References Cited

U.S. PATENT DOCUMENTS

| | | | | |
|---|---|---|---|---|
| 4,649,483 A | * | 3/1987 | Dixon, Jr. ............ | G01N 23/046 250/256 |
| 4,868,751 A | * | 9/1989 | Dogru .................... | G01N 15/08 702/12 |
| 5,086,643 A | * | 2/1992 | Marek ................ | G01N 15/0826 73/38 |
| 5,297,420 A | * | 3/1994 | Gilliland ................ | G01N 15/08 73/38 |

(Continued)

OTHER PUBLICATIONS

Santagati et al. "Laboratory Comparison of Natural Fractures and Induced Fracture Permeability Variations Under Simulated Dynamic Reservoir Conditions," International Petroleum Technology Conference, Beijing, China, Mar. 22, 2019 (Year: 2019).*

(Continued)

*Primary Examiner* — John Fitzgerald
(74) *Attorney, Agent, or Firm* — Bracewell LLP; Constance G. Rhebergen; Christopher L. Drymalla

(57) ABSTRACT

Fracture porosity and permeability variations with increasing effective stress, are measured and determined by laboratory testing of rock cylindrical core plugs of various types (carbonate, silico-clastic, shale, e.g.) and dimensions. The testing can be implemented for both natural and induced fractures propagating axially in the rock core plug. The testing begins with initial testing, sample preparation and obtaining measurements on an intact plug to define matrix properties in the rock core plug. A rock core plug with defined matrix properties is then after further preparation, subjected to an axial shear fracture (natural or induced) propagating through its body. Measurements are then obtained from the plug with an axial shear fracture (natural or induced) propagating through its body to determine fracture properties.

9 Claims, 7 Drawing Sheets

(56) References Cited

U.S. PATENT DOCUMENTS

| | | | |
|---|---|---|---|
| 7,830,744 | B2 | 11/2010 | Wu et al. |
| 7,970,544 | B2 | 6/2011 | Tang et al. |
| 8,005,618 | B2 | 8/2011 | Gzara |
| 9,507,047 | B1* | 11/2016 | Dvorkin ................. G01V 5/101 |
| 9,715,026 | B2 | 7/2017 | Ejofodomi et al. |
| 10,261,204 | B2* | 4/2019 | Boot ......................... G06T 7/37 |
| 10,571,605 | B2* | 2/2020 | Crawford ............. G01V 99/005 |
| 2012/0151998 | A1* | 6/2012 | Willberg ................ G01N 1/286 73/38 |
| 2014/0119497 | A1* | 5/2014 | Guzman .................. G01N 1/36 378/5 |
| 2015/0331145 | A1* | 11/2015 | Grachev ................. G06F 17/10 703/2 |
| 2016/0187509 | A1* | 6/2016 | Boot ..................... G06T 3/4038 382/109 |
| 2016/0326845 | A1* | 11/2016 | Djikpesse .............. G06Q 50/02 |
| 2017/0275970 | A1 | 9/2017 | Crawford et al. |
| 2017/0316128 | A1* | 11/2017 | Huang .................... G06F 30/20 |
| 2019/0226970 | A1* | 7/2019 | Dusterhoft ............. E21B 49/00 |
| 2021/0063325 | A1* | 3/2021 | Drenzek ............... G06T 11/008 |

OTHER PUBLICATIONS

A. Keller, High Resolution, Non-destructive Measurement and Characterization of Fracture Apertures, Int. J. Rock Mech. Min. Sci., 1998, vol. 35, No. 8, pp. 1037-1050, Pergamon.

Da Huo et al, A Calibration-free Approach for Measuring Fracture Aperture Distributions Using X-ray Computed Tomography, GEOSPERE, 2016, vol. 12, No. 2, p. 558-571.

G. N. Boitnott, Use of Complex Pore Pressure Transients to Measure Permeability of Rocks, SPE 38717, New England Research, Inc., 1997.

Milsch et al., An Experimental and Numerical Evaluation of Continuous Fracture Permeabilty Measurements During Effective Pressure Cycles, 2016, p. 109-115, International Journal of Rock Mechanics & Mining Sciences 89.

Q Lei, The Use of Discrete Fracture Networks for Modelling Coupled Geomechanical and Hydrological Behaviour of Fractured Rocks, Computers and Geotechnics 85 (2017) pp. 151-176.

Song et al., Morphological Characteristics of Microscale Fractures in Gas Shale and its Pressure-Dependent Permeability, Feb. 2017, SB-25-SB31, Interpretation.

Yuedu Chen et al, Experimental Study on the Effect of Fracture Geometric Characteristics on the Permeability in Deformable Rough-Wailed Fractures, International Journal of Rock Mechanics & Mining Sciences 98, Jul. 2, 2017, pp. 121-140, Elsevier Ltd.

Zimmerman et al., Compressibility of Porous Rocks, 1986, Journal of Geophysical Research, vol. 91, No. B12, pp. 12,765-12,777.

Ilgen, Anastasia G. et al.; "Shales at all scales: Exploring coupled processes in mudrocks" Earth-Science Reviews, 166 (2017) pp. 132-152.

International Search Report & Written Opinion for International Application No. PCT/US2020/041264, dated Sep. 21, 2020; pp. 1-18.

ASTM International "Standard Test Method for Splitting Tensile Strength of Intact Core Specimens" D3967-08, Jul. 1, 2008; pp. 1-4.

ASTM International; "Standard Practices for Preparing Rock Core as Cylindrical Test Specimens and Verifying Conformance to Dimensional and Shape Tolerances" D4543-08, Jan. 1, 2008; pp. 1-9.

ASTM International; "Standard Test Methods for Compressive Strength and Elastic Moduli of Intact Rock Core Specimens under Varying States of Stress and Temperature" D7012-14, May 1, 2014, pp. 1-9.

* cited by examiner

LABORATORY MEASUREMENT OF DYNAMIC FRACTURE POROSITY AND PERMEABILITY VARIATIONS IN ROCK CORE PLUG SAMPLES

BACKGROUND OF THE INVENTION

1. Field of the Invention

The present application relates to laboratory testing of rock core plug samples from subsurface reservoir formations to measure geomechanical properties of the formation.

2. Description of the Related Art

A fractured reservoir is one in which occurring fractures have a significant effect on fluid flow. Natural fractures provide essential porosity ($\varphi$) and permeability (k) to assist hydrocarbon production. In order to rigorously model reservoir performance in this type of reservoir, it is important to measure fracture porosity and permeability variations under dynamic stress conditions.

Porosity and permeability are petrophysical properties of rock formations in subsurface reservoirs. These properties differ over the production life of the reservoir and are affected by changes in stress imposed on the subsurface rock during production from the reservoir. The changes in these petrophysical properties present important and valuable information in order to assess how best to produce and develop hydrocarbons from the reservoir.

So far as is known, testing to determine the petrophysical properties has been done in separate tests in wells performed in-situ in the reservoir. One form of such tests, commonly referred to as "well testing", was pressure transient testing to obtain measures in response to hydraulic pressure changes applied to the formation from fluids in the well. Well testing usually provides permeability information on large volumes of rock and may not discriminate between individual fractures. A second type of such tests, commonly referred to as "well logging", were well logging measurements obtained during well logging runs by logging equipment sondes lowered into the well bores. Well logging provides indirect measurements that should be calibrated against a direct laboratory measurement. Both types of tests were expensive and time-consuming. Further, production of hydrocarbons from the well was interrupted during such testing. In addition, the separate testing for porosity and permeability did not provide measures of these two petrophysical properties from the same rock test sample.

SUMMARY OF THE INVENTION

Briefly, the present invention provides a new and improved method of laboratory measurement of dynamic variations in petrophysical properties of a subsurface formation as a result of changes in stress applied to a core plug rock sample obtained from a location of interest in the subsurface formation. Computerized tomography is performed on the core plug rock sample to determine homogeneous density distribution in the rock sample. A measure of a relationship between matrix porosity sensitivity and matrix permeability sensitivity of the rock sample is then determined. An axially extending shear fracture is propagated through the rock sample to form a split core plug composed of fracture halves of the rock sample. The fracture halves of the split core plug are shifted axially with respect to each other to simulate displacement during in-situ fracture of the formation rock. The fracture shifted halves of the split core plug are then joined together to form a joined split plug. A measure is then determined of sensitivity to stress of the fracture porosity and the fracture permeability of the core plug rock sample.

The present invention also provides a new and improved method of laboratory measurement of a relationship between matrix porosity sensitivity and matrix permeability sensitivity as a result of changes in stress applied to a core plug rock sample obtained from a location of interest in a subsurface formation. Computerized tomography is performed on the core plug rock sample to determine homogeneous density distribution in the rock sample. A pore volume compressibility test of the rock sample is performed to determine sensitivity to stress variations of matrix porosity of the rock sample. A stress-dependent permeability test of the rock sample is performed to determine sensitivity to stress variations of matrix permeability of the rock sample. A measure is then formed of a relationship between matrix porosity sensitivity and matrix permeability sensitivity of the rock sample.

The present invention further provides a new and improved method of laboratory measurement of dynamic variations in petrophysical properties of a subsurface formation as a result of changes in stress applied to a split core plug rock sample obtained from the location of interest. An axially extending shear fracture is formed through a core plug rock sample to form a split core plug composed of fracture halves of the core plug rock sample. The fracture halves of the split core plug are shifted axially with respect to each other to simulate displacement during in-situ fracture of the formation rock. The shifted fracture halves of the split core plug are joined together to form a joined split plug and fracture porosity of the joined split plug is determined. A pore volume compressibility test of the joined split plug is performed to determine sensitivity of the matrix porosity of the split plug to stress variations, and a stress-dependent permeability test of the joined split plug is performed to determine sensitivity of matrix permeability of the split plug to stress variations.

DETAILED DESCRIPTION OF THE PREFERRED EMBODIMENTS

Introduction

Figure 1:
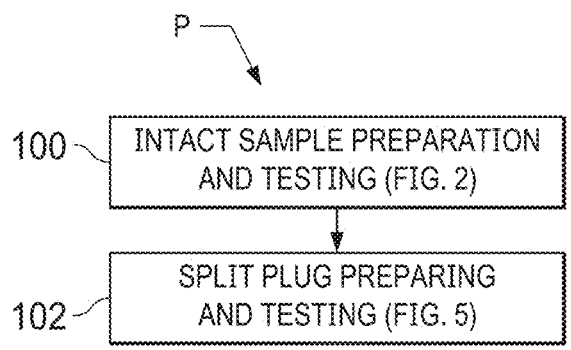
FIG. 1 is a schematic diagram of a method of laboratory measurement of dynamic fracture porosity and permeability variations in rock core plug samples according to the present invention.

In the drawings, the letter P designates generally a high level laboratory workflow and the associated procedures performed according to the present invention to measure for evaluation petrophysical parameters of fracture porosity ($\varphi$) and permeability (k) of rock cylindrical core plugs obtained from wells in subsurface formations at locations of interest. The present invention provides methods for laboratory measurement of dynamic fracture porosity and permeability variations in the rock core plugs with increasing effective stress. The rock core plugs may be of various geological character (carbonate, silico-clastic, shale, etc.) and typical dimensions for rock cylindrical core plugs obtained from wells.

The present invention is adapted for evaluation of petrophysical parameters of fracture porosity ($\varphi$) and permeability (k) on core plug samples with either or both natural and induced fractures propagating axially in the plug. As shown in FIG. 1, the workflow P is composed of two test sequences. The first test sequence is a rock plug sample preparation and testing sequence 100 of the workflow P of FIG. 1. The rock plug sample preparation and testing 100 is shown in more detail in FIG. 2. Testing Sequence 100 involves sample preparation, and measurements performed on an intact plug to define the matrix properties, as will be described.

Figure 5:
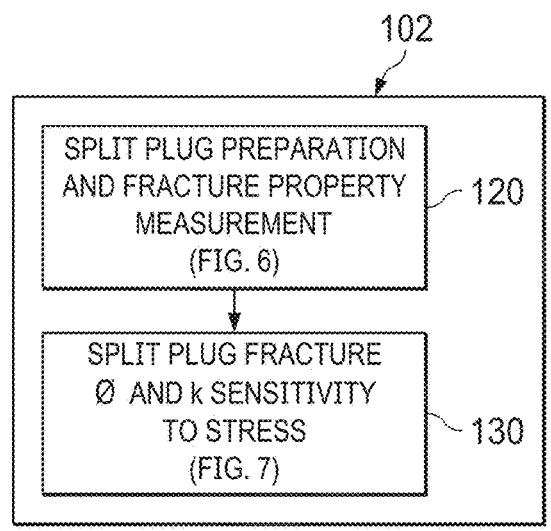
FIG. 5 is a schematic diagram of a split plug preparation and testing according to the method of FIG. 1.

The workflow P also includes a split plug preparation and testing as indicated at 102 in FIG. 1. The split plug preparation and testing 102 provides for defining fracture properties of the plug. As shown in FIG. 5, the split plug preparation and testing 102 involves sample preparation and performance of measurements on a plug with an axial shear fracture (natural or induced) propagating through its body.

Testing Sequence 100: Intact Plug (Matrix)

The rock plug sample preparation and testing sequence 100 (FIGS. 1-4) involves preparation and the measurements performed on an intact plug. The study plug should be selected to be representative of the formation matrix. As an example, 1.5 diameter carbonate specimens with a length of approximate 2.0" have been tested.

Figure 2:
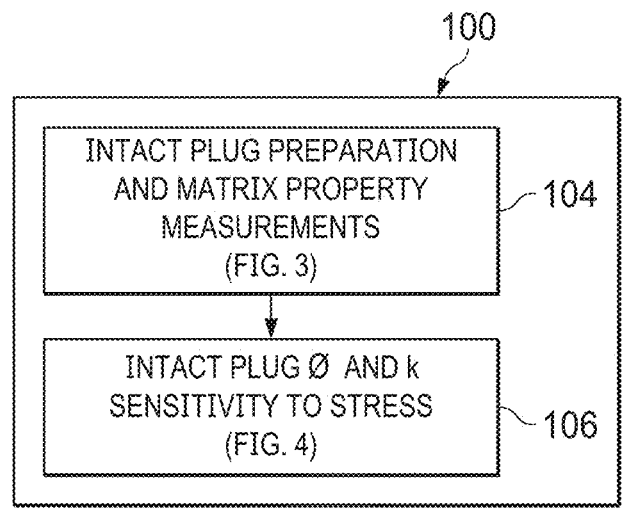
FIG. 2 is a schematic diagram of rock plug sample preparation and testing according to the method of FIG. 1.
Figure 3:
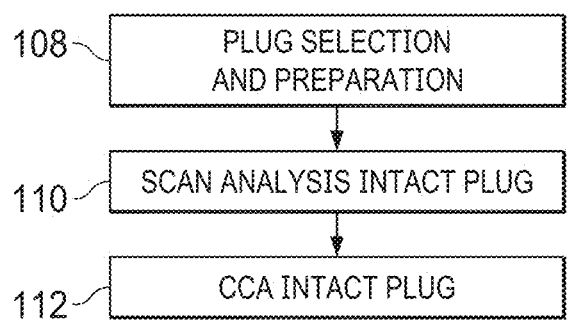
FIG. 3 is a schematic diagram of intact plug preparation and matrix property measurement according to the method of FIG. 2.

Step 104: Preparation and Property Measurement (FIGS. 2 and 3)

Step 104 involves preparation and matrix property (porosity ($\varphi$), permeability (k)) measurement of the intact rock plug sample. Step 104 begins with step 108 which is shown in FIG. 3.

Step 108: Plug Selection and Preparation (FIG. 3)

During plug selection in step 108, a cylindrical specimen of the target formation is selected from existing sets or plugged from a whole core. Selection is based on lithology and petrophysical properties (density, porosity, permeability) as defined by the well logs and from visual inspection of the whole core. Consideration should be given that an objective of the measurements is to study the behavior of natural shear fractures embedded in the existing rock matrix of the study reservoir. Plugs with existing natural shear fractures may be selected as well, provided that the shear fracture develops axially and connects the bottom and top surfaces of the plug. Also, for each plug that includes a natural shear fracture an intact benchmark plug with a matrix representative of the matrix of the fractured plug must be available.

Plug preparation according to step 108 is performed by preparing the plug for testing following conventional testing procedures. Preferably ASTM Standard D4543-08 is the procedure used. Preparation indicates a length-to-diameter ratio (L/D) for the core specimens of 2.0 to 2.5. Plugs selected may have a lower L/D ratio unless additional mechanical parameters (elastic moduli) of the plug such Young's modulus and Poisson's ratio are to be measured. Procedures for the determination of the elastic moduli on cylindrical specimens of rock are discussed in ASTM Standard D-7012-14.

Step 110: CT Scan Analysis of the Intact Plug

Step 110 is performed after step 108 and takes the form of a computerized tomographic (CT) scan to analyze internal structure of the plug matrix and verify whether discontinuities or high/low density inclusions are detected. A number of commercially available computerized tomographic scanners may be used for this purpose. Various types of CT scan analysis (examples include: medical CT scan, micro-CT scan and the like) are available.

Figure 8:
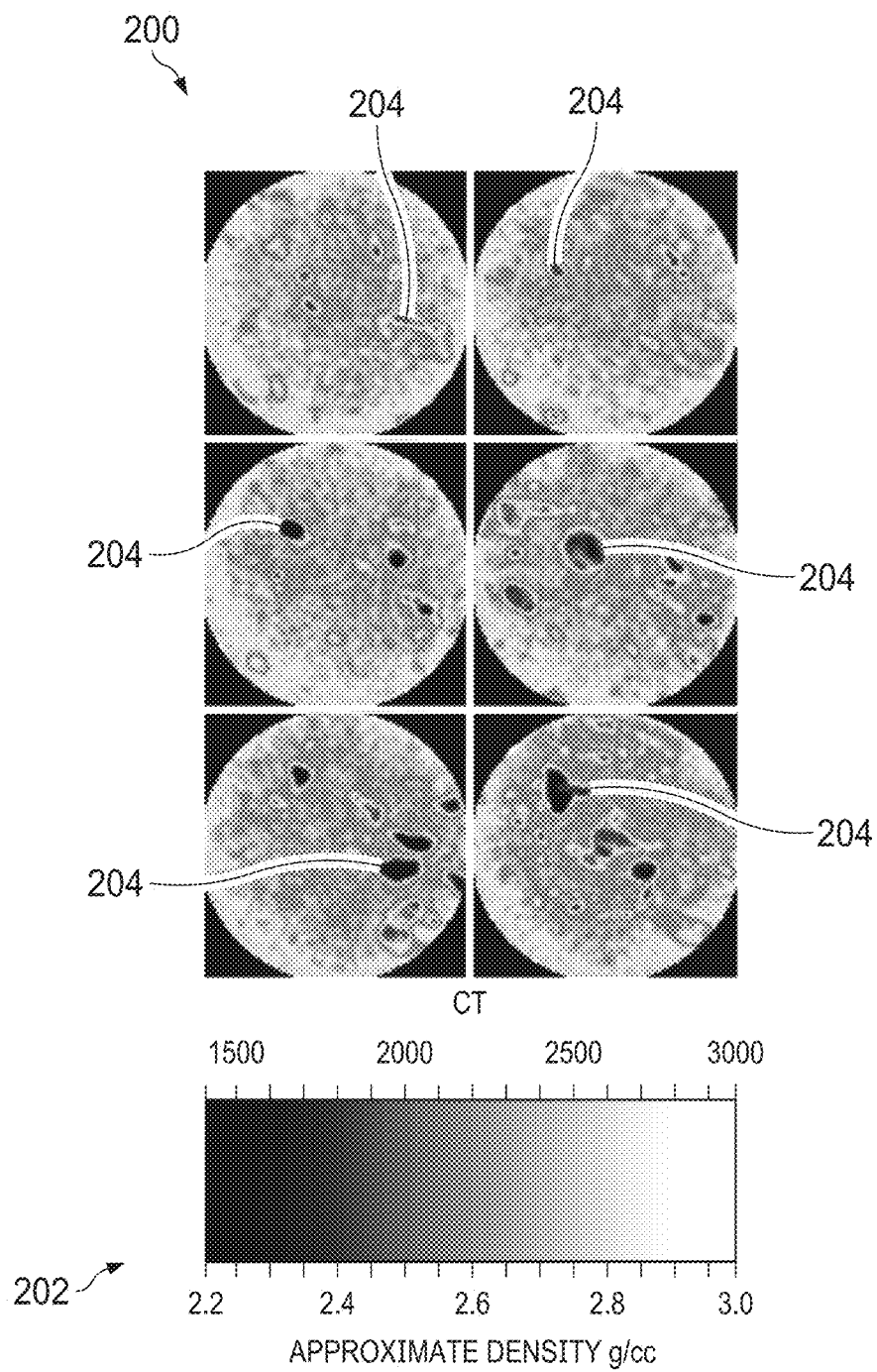
FIG. 8 is a display of an example computerized tomography scan analysis according to the present invention of a core plug rock sample with accompanying density scale key.

FIG. 8 is an example display in a black and white image of color scan images of CT analysis results of an example plug. FIG. 8 shows at 200 density of slices of a study plug, a color scale 202 provides a density or color quantification key (in this case g/cc (grams per cubic centimeter)). The presence of low density inclusions (most likely vugs) within the matrix of the example plug is indicated at 204 in several places in the sample plug. Plugs that indicate the presence of vugs or discontinuities as indicated generally by dark spots in the CT images such as shown in FIG. 8 should be discarded. These plugs do not have a homogeneous density distribution and a continuous structure.

First, the geometry of the plug is modified by induced fractures during subsequent steps. The modification is made under the assumption plug matrix petrophysical properties (density, porosity, etc.) will not be affected. A heterogeneous density distribution or the presence of discontinuities in the original plug would contradict such an assumption. Variations of the relative weight that heterogeneities or discontinuities might have on the plug matrix petrophysical properties after its geometry is modified would indicate the plug matrix properties are not the same before and after the modification.

Second, the induced fracture should propagate approximately axially and should not have irregular branching or connect to other discontinuities. The presence of heterogeneities/discontinuities may affect the propagation of the fracture within the plug. While this is an event that may occur naturally in the in-situ rock fracture propagation as well, it is not ideal in a laboratory environment where the aim is to have a controlled fracturing process. Only plugs with a homogeneous matrix and no discontinuities (FIG. 9) should be selected for the purposes of the present invention.

Figure 9:
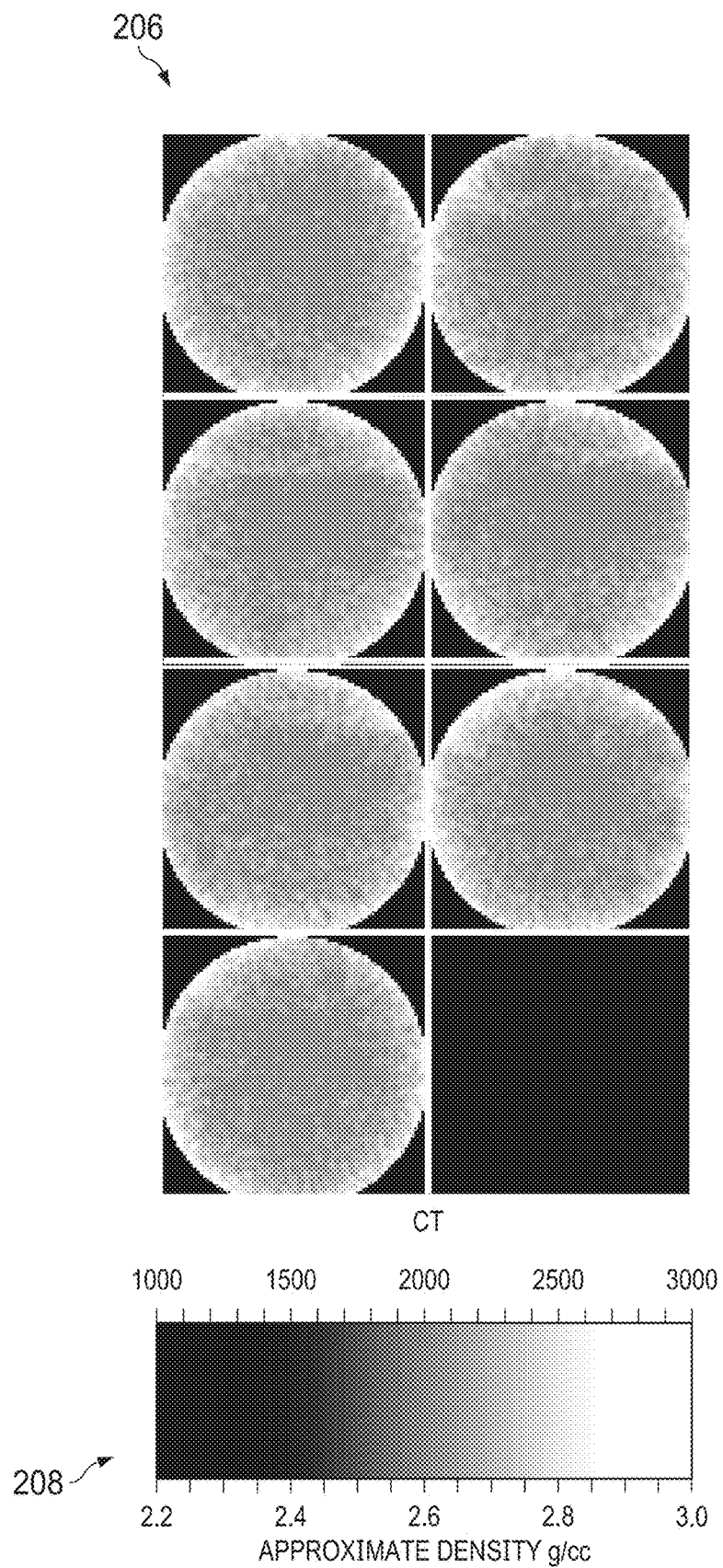
FIG. 9 is another display of an example computerized tomography scan analysis according to the present invention of a core plug rock sample with accompanying density scale key.

FIG. 9 is an example display 206 in a black and white image of color scan images of CT analysis results of an example plug showing of a homogeneous study plug. A density scale 208 indicates approximate density values. The density of the plug in FIG. 9 is indicated by the CT analysis to be substantially homogeneous. Such a plug is one that should be considered fit for the purposes of further testing.

Step 112: Conventional Core Analysis of the Intact Plug

Referring to FIG. 3, step 112 is performed to obtain the measurements of basic petrophysical properties on the intact plug (matrix). The petrophysical properties obtained may include, as a minimum:
Sample dimensions (L, D)
Sample weight (dry/saturated)
Porosity ($\varphi$)
Permeability (k)
Grain Density The methodologies to measure the petrophysical properties listed are standard Conventional Core Analysis (CCA) techniques widely used in the industry.

Step 106: Intact Plug Stress Sensitivity Testing

After conventional core analysis during step 112 of intact plug property measurement 104, intact plug stress sensitivity testing according to step 106 is performed.

During step 108 discussed previously, the plug location was selected based on the well log petrophysical analysis. Now, the same properties are measured directly on the plug to confirm that the sample is indeed representative of the study interval in the formation rock. Plugs whose petrophysical properties are abnormal or somehow different than expected may be discarded at this stage.

Matrix (intact plug) porosity and permeability are extremely important as they will be required in the final interpretation of the test results to determine the fracture porosity and permeability according to the present invention.

Determination of the porosity and permeability sensitivity to stress for the intact plug (matrix) is performed by means of testing in a servo-controlled rock mechanics triaxial apparatus. The stress range for the tests included in this phase are defined based on estimates of the state of stress existing in the reservoir over its entire production life, from the initial (virgin) state to abandonment.

Step 114: Pore Volume Compressibility (PVC) Test

Figure 4:
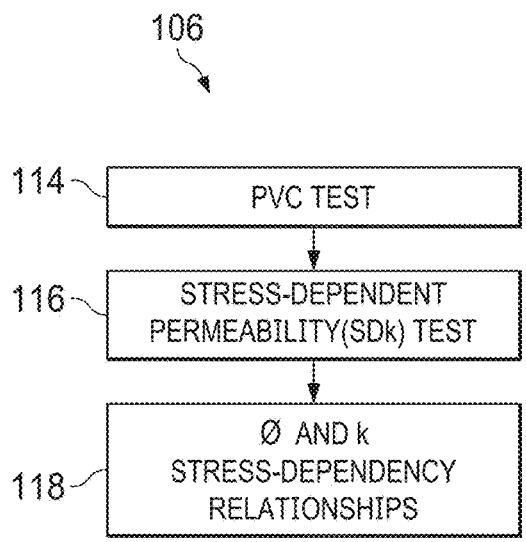
FIG. 4 is a schematic diagram of measurement of intact plug porosity and permeability variation with stress according to the method of FIG. 2.

During step 114 (FIG. 4, the sensitivity to stress of the matrix porosity (intact plug) is determined. Pore Volume Compressibility (PVC) tests are performed and the variation of the pore volume with an evolving state of stress is measured. This can be accomplished in a variety of ways. Details about the different types of compressibility measurements that may be performed are discussed in R. W. Zimmerman, et al, "Compressibility of Porous Rocks", Journal of Geophysical Research, Vol. 91, No. B12, pp. 12,765-12, 777, 1986.

A volume of water expelled by the specimen under increasing confining pressure is measured. Further, it is assumed that the volume of expelled water at time $t_1$ is equal to the total variation in pore space from time to 0 (start of the experiment) to $t_1$. This procedure is performed to determine a hydrostatic pore volume compressibility at changing confining pressure Cpc as defined in Zimmerman.

The samples are saturated in 10% NaCl brine under vacuum to remove all air. Then, the samples are mounted on transducers and placed in the pressure vessel of the testing machine. A convenient pore pressure of 3 MPa (MegaPascal) was applied to the pore fluid saturating the sample. The sample was then loaded hydrostatically under uniform three-dimensional pressure stress (s1=s2=s3) up to the desired pressure level and then unloaded back. Then pore strain (correspondent to the pore volume variation) is computed from the volume curve of fluid expelled from the rock specimen as the confining pressure is increased, for example during the loading cycle.

The measurements may be performed not only under hydrostatic conditions (s1=s2=s3), but also in a triaxial state of stress (s1>s2=s3) with a piston axially loading the cylindrical sample up to a specific level.

The dynamic state of stress of the experiment must be such that the plug specimen undergoes only elastic deformation with no permanent strain during the test. If any indication is received that the plug experienced plastic (non-recoverable) deformation during the test, then the specimen should be discarded. This is because the measurement conducted in the subsequent stages of the testing may be affected by the altered structure of the rock matrix in a non-linear fashion.

Step 116: Stress-Dependent Permeability (SDk) Test

Step 116 of stress-dependent permeability testing determines the sensitivity to stress of the matrix permeability of the intact plug. A series of permeability measurements are performed at various states of stress defined as stations. The measurement stations are selected in order to cover the same stress interval over which the PVC test during step 114 was conducted.

The samples during step 116 are also saturated in 10% NaCl brine under vacuum to remove all air. Then, the samples are mounted on transducers and placed in the pressure vessel of the testing machine. A convenient pore pressure of 3 MPa is applied to the pore fluid saturating the sample. The sample was then loaded to the first one of the required states of stress (hydrostatic or triaxial) and the permeability (k) is measured. The state of stress is then modified to the next station and the measurement of permeability is repeated until all of the planned stations are completed.

The permeability measurements may be performed under steady state or unsteady state conditions. The pressure response at the downstream end of the plug is interpreted automatically such as by techniques described in G. N.

Boitnott, "Use of Complex Pore Pressure Transients to Measure Permeability of Rocks", SPE 38717, 1997.

Step 118: Porosity and Permeability Stress-Dependency Relationships

Performance of step 118 defines relationships between the matrix porosity and permeability and the state of stress based on the results of the tests performed in steps 114 and 116. Matrix porosity is usually sensitive to stress variations and the relationship may be approximated by a logarithmic fitting. The relationship between matrix permeability and the state of stress is more complex and may change in nature for different stress intervals. An example display of a specimen with permeability almost insensitive to hydrostatic stress variations is given in FIG. 10.

Figure 10:
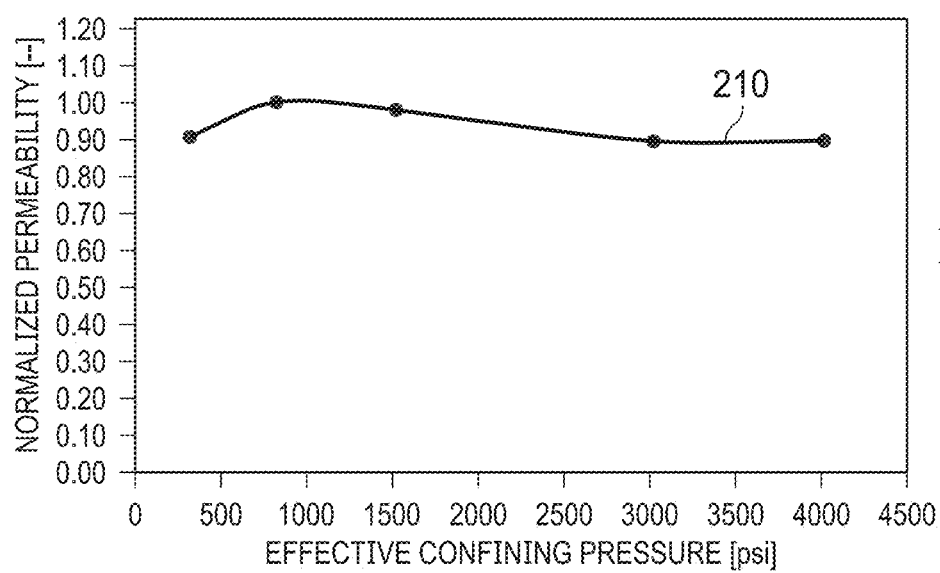
FIG. 10 is a display of normalized permeability of an intact core plug as a function of pressure.

FIG. 10 can be seen to indicate at 210 permeability as a function of applied pressure (in psi or pounds per square inch) showing little or no sensitivity to variations in hydrostatic loading large effective stress interval (250-4,000 psi) of applied pressure is indicated. The matrix permeability is normalized against the highest permeability measured along the test. A slightly positive feedback is observed between 500 and 1,500 psi.

The definition of the matrix porosity/stress and permeability/stress relationships during step 118 allows the determination of the correction factors for the calculation of the fracture porosity and permeability in further testing, as will be described.

Step 102: Split Plug (Fracture)

Figure 6:
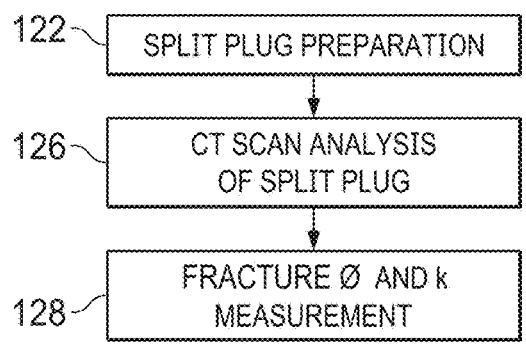
FIG. 6 is a schematic diagram of a split plug preparation and fracture property measurement according to the method of FIG. 5.
Figure 7:
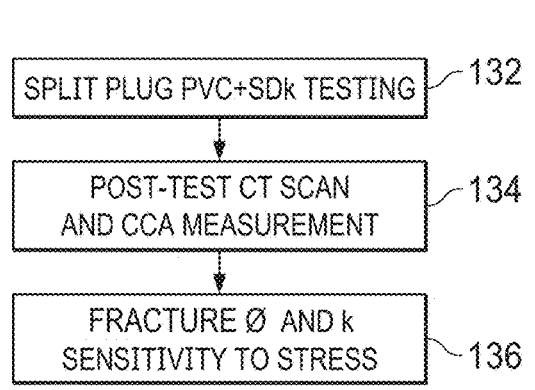
FIG. 7 is a schematic diagram of measurement of the split plug porosity and permeability variation with stress according to the method of FIG. 5.

Split plug preparing and testing step 102 (FIGS. 1 and 5-7) includes step 120 (FIGS. 5 and 6) related to the preparation of a split plug and fracture property measurement. According to the present invention, a split plug is a plug with an approximately homogenous and continuous matrix as described in step 100 with mode II fracture propagated axially connecting the two ends of the specimen. Step 130 (FIGS. 5 and 7) obtain measurements performed on the same split plug to determine the sensitivity of the fracture porosity and permeability to variation in the stress state. The plug subjected to step 102 is one which has been processed according to step 100 as an intact plug. Alternatively, a plug with a natural fracture extending from top to bottom is selected for step 102 to be used. This may be done if an intact plug with an identical matrix but no fractures went through all the relevant tasks included in step 100.

Step 120 Split Plug Preparation and Fracture Property Measurement

Split plug preparation and fracture property measurement 120 (FIG. 6) typically begins with splitting the plug during step 122. As noted, however, a plug with a natural fracture may be used under appropriate conditions.

Step 122: Split Plug Preparation

During step 122, a fractured cylindrical rock plug is prepared for testing into a servo-controlled triaxial machine. The fracture should be of the Mode II type (shear fracture) and extend axially across the sample. It should also connect the top and the bottom of the specimen.

Fracture modes are defined by the way that force is applied to cause a crack to propagate in the sample plug. Such a fracture may be of three different types. Two of those types: Mode I fractures (propagated by a tensile stress normal to the plane of the crack), and Mode II fractures (propagated by a shear stress acting parallel to the plane of the crack and perpendicular to the crack front), are of interest for the present invention.

Natural fractures existing within the earth crust are assumed to be of the Mode II type (shear fractures). Mode I type fractures are usually induced fractures. Also, Mode II fractures are self-propped fractures meaning that the relative movement of the two halves of the fracture ensures that the topographies of opposite planes in the plug sample do not match. This in turn increases the hydraulic conductivity of the fracture even at increasing confining pressure. On the other hand, Mode I fractures are not self-propped, and their conductivity is limited and may not contribute to the overall permeability of the rock.

Plugs already containing a natural Mode II fracture with the characteristics described previously may be selected for this phase (assuming a plug with no fracture and with the same matrix is tested according to step 100). Otherwise, a Mode II fracture should be propagated through an intact plug for which the step 100 testing is already completed.

The procedure to fracture an intact plug during step 122 involves two main sequences. Mode I axial tensile fracture is first created. The Mode I fracture is then transformed into a Mode II fracture. This is done by shifting the two halves of the plug past each other as to simulate the shear displacement characterizing Mode II fractures.

Step 122: Forming Split Plug

Step 122 simulates and approximates the natural rupturing process of the in-situ (underground) rock. The cylindrical plug is split under tension along its axis to form an axial tensile fracture plane. A cylindrical plug specimen 220 (FIG. 11) is placed in a servo-controlled loading device L and the load is applied at a constant rate until the axial tensile fracture is created. The procedure is preferably performed according to ASTM Standard D3967-08.

Figure 11:
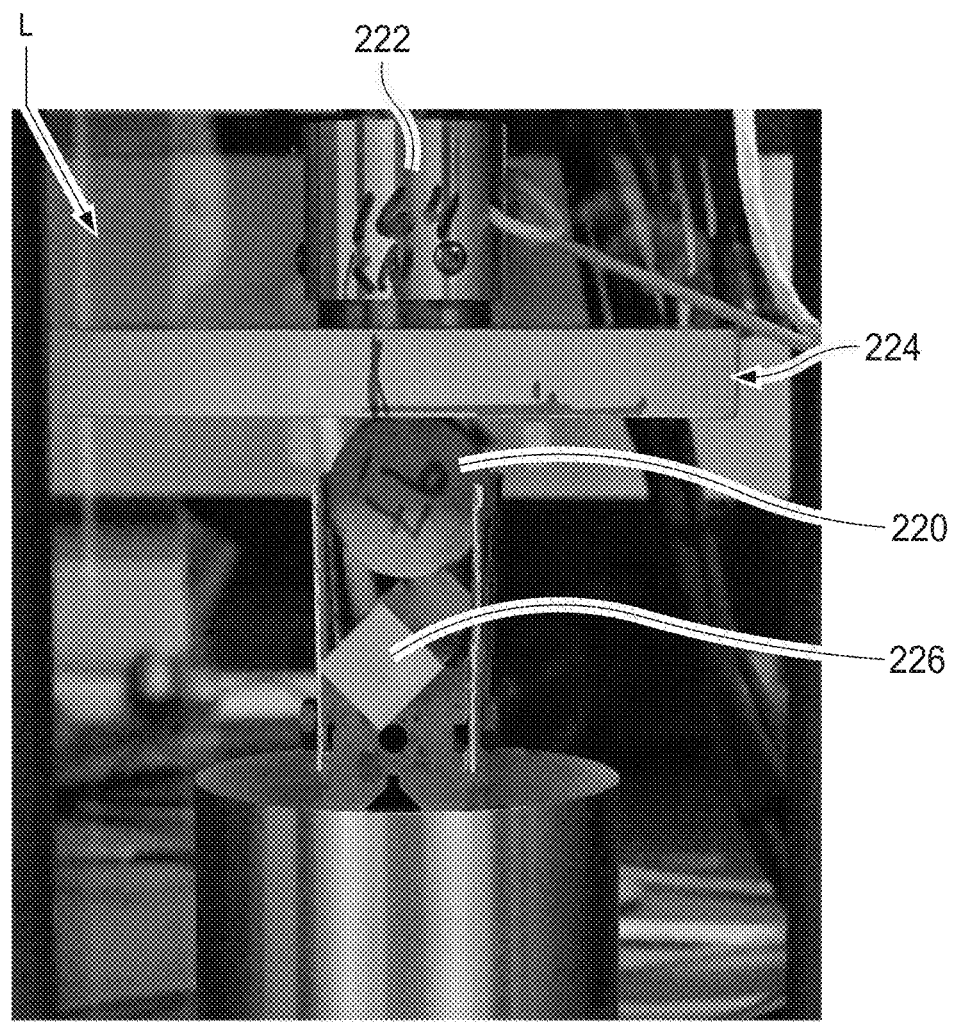
FIG. 11 is a display of an arrangement for forming a split core plug from an intact core plug according to the present invention.

According to the present invention, step 122 has two main differences with procedure described in ASTM Standard D3967-08, as shown in FIG. 11. The length of the specimen 220 is higher than the diameter of loading piston 222. For this reason a plate 224 of suitable dimensions is placed between the piston 222 and the specimen 200 in order to spread the load over the entire length of the plug axis. The plug 220 must also lie on its axis on a sharp wedge 226 in order to control the propagation of the fracture and prevent branching. The sharpness of the edge 226 should also prevent the formation of a groove along the side of the specimen.

A specimen plug with a branching fracture is not ideal for testing with the present invention. With a plug having a branching fracture, it is not possible to discriminate the contribution of different branches to the overall fracture permeability. A plug with a branching fracture prevents establishment of a relationship between each individual fracture plane properties and the state of stress.

Figure 12:
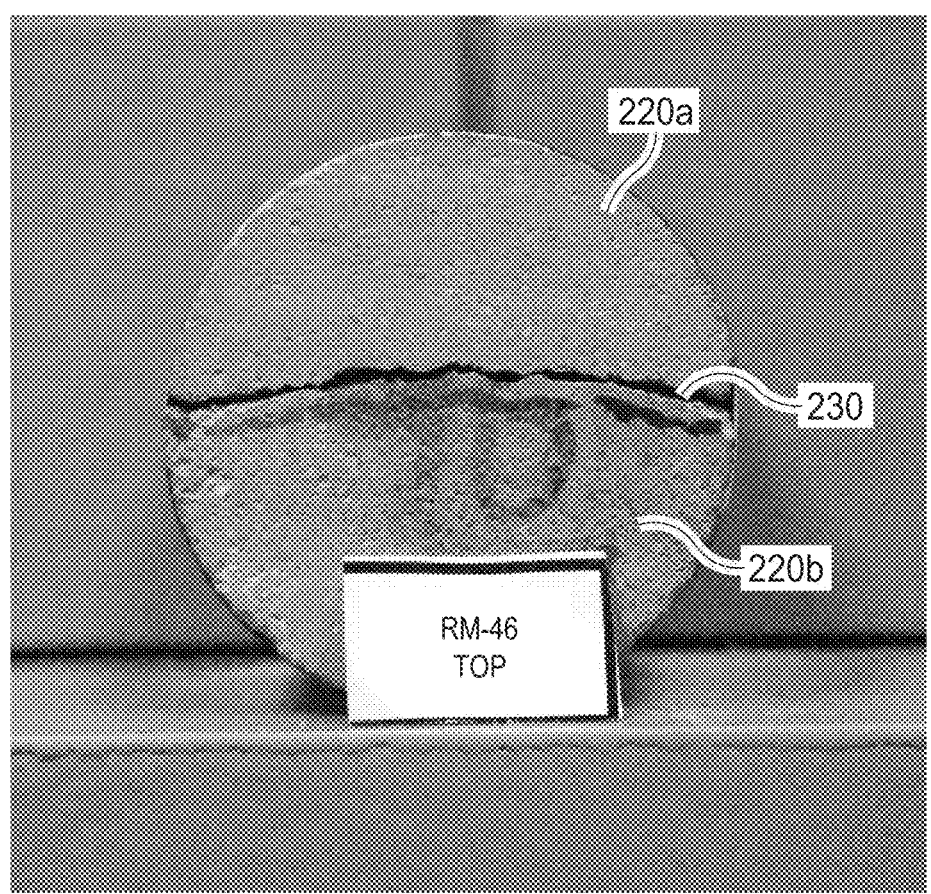
FIG. 12 is a display of a split core plug formed according to the present invention for performing petrophysical property measurements of the core plug.

Next during step 124, the two resultant fracture halves (faces) 220a and 220b (FIG. 12) are slid past each other either by hand or mechanically to simulate the displacement undergone naturally when a shear stress component acts on the rock during the in-situ fracturing process. The fracture now becomes self-propped due to the asperity topography on the two halves not matching along a fracture plane 230 (FIG. 12).

While this laboratory process replicates the source of the natural Mode II fractures conductivity (that is, the mismatch between the topographies on the fracture plane), one major discrepancy between the laboratory testing and the natural in-situ process must be taken into account. There is a difference in the strength of the topographic asperities, the laboratory ones being much weaker than those created in-situ. The reason for this difference apparently is due to the fact that the laboratory asperities are created on surface and at ambient conditions (no confining pressure), while the reservoir fractures responsible for downhole conductivity form within the deep earth crust state of stress.

Laboratory asperities deform plastically at relatively low confining pressures. This has been observed in other studies as well (See H. Milscuh, et al, "An Experimental and Numerical Evaluation of Continuous Fracture Permeability Measurements During Effective Pressure Cycles", Int. J. Rock Mech. Min. Sci. Vol. 89, pp. 109-115, 216). Hence, the loss of permeability experienced by the laboratory fracture during testing is non-recoverable. Note that if a plug with a Mode II natural fracture is selected for step 102, then the loss of permeability experienced by the fracture during testing may be recoverable instead.

To complete the split plug preparation during step 124, the excessive rock volume protruding from the plug ends due to the shifting must be ground off to recover the cylindrical shape required for testing in a triaxial apparatus. This is performed by plug preparation according to ASTM Standard D4543-08. Teflon tape may be used to keep the two halves of the specimen together during the preparation. The processes of splitting, shifting and grinding modify the plug geometry and the total volume of the matrix decreases. However, in preparation for further testing during step 126 and 128, it is assumed that the overall porosity and permeability of the split plug matrix are not affected.

Step 126: CT Scan Analysis of Split Plug

During step 126, computerized tomographic (CT) scanning analysis of the split plug is performed to visualize geometry of the shear fracture and to confirm that the structure of the matrix of the split plug has not been affected by the splitting, shifting and grinding operations performed during step 124.

The CT scan analysis during step 126 can confirm whether the fracture actually developed along a single plane or whether branching occurred. Branching could affect the fracture permeability measurement. In the event of branching, the plug may be discarded if it is believed that the contribution of the additional branches to the overall plug permeability may be relevant and could not be discriminated.

CT scanning during step 126 also may be used to calculate fracture aperture, if required. Various methodologies for this have been published. (See A. Keller, "High Resolution, Non-destructive Measurement and Characterization of Fracture Apertures", Int. J. Rock. Mech. Min. Sci., Vol. 35, No. 8, pp. 1037-150, 1998; D. Huo, et al, "A Calibration-free Approach for Measuring Fracture Aperture Distributions Using X-ray Computed Tomography", Geosphere, Vol. 12, No. 2, 2016; Z. Song, et al, "Morphological Characteristics of Microscale Fractures in Gas Shale and its Pressure-Dependent Permeability, Interpretation, February, 2017).

If a specimen with a natural fracture is selected for step 126, then the CT scan analysis at this stage is also used to verify the structure of the matrix according to step 110. A plug may be discarded if it is found that the matrix structure is not suitable or if it is not an analog of the matrix of the corresponding intact plug.

Step 128: Fracture Porosity and Permeability Measurement

Step 128 performed is to obtain the measurements of basic petrophysical properties of the split plug (fractured). These petrophysical properties include at least the following:

Sample dimensions (L, D)
Sample weight (dry/saturated)
Total Porosity ($\varphi$)

The methodologies to measure the petrophysical properties listed previously are the same employed for step 112 and performed in a like manner. Based on the total plug porosity (matrix+fracture) and on the matrix porosity measured in step 112 a fracture porosity can be derived.

$$\varphi_{Frac} = \varphi_{Tot} - \varphi_{Matrix} \qquad (1)$$

The fracture volume based on the calculated fracture porosity is used as initial pore volume value for subsequent PVC testing, as will be described.

Step 130: Split Plug Fracture Stress Sensitivity

Determination of the fracture porosity and permeability sensitivity to stress during step 130 (FIG. 5) is performed by testing in a servo-controlled rock mechanics triaxial apparatus. The stress range for the tests included in step 130 is the same as performed during step 106 for the matrix (intact plug) tests.

Step 132: Split Plug PVC+SDk Testing

Step 132 is performed to determine the sensitivity to stress of the split plug fracture porosity and permeability. During step 132, the split plug is subjected in a timed sequence (FIG. 13) in a succession of increases or ranges 230 in confining pressure. During step 114 and 116 described previously, the two measurements (PVC and SDk tests) are performed separately. The type of deformation expected during steps 114 and 116 is only of the recoverable (elastic) type. In the case of a split plug this may not be the case as the fracture plan asperities responsible for propping of the fracture, and porosity and permeability of the fracture may be expected to deform plastically. For this reason, the two measurements should now be performed during step 132 together and concurrently within the same loading cycle.

Figure 13:
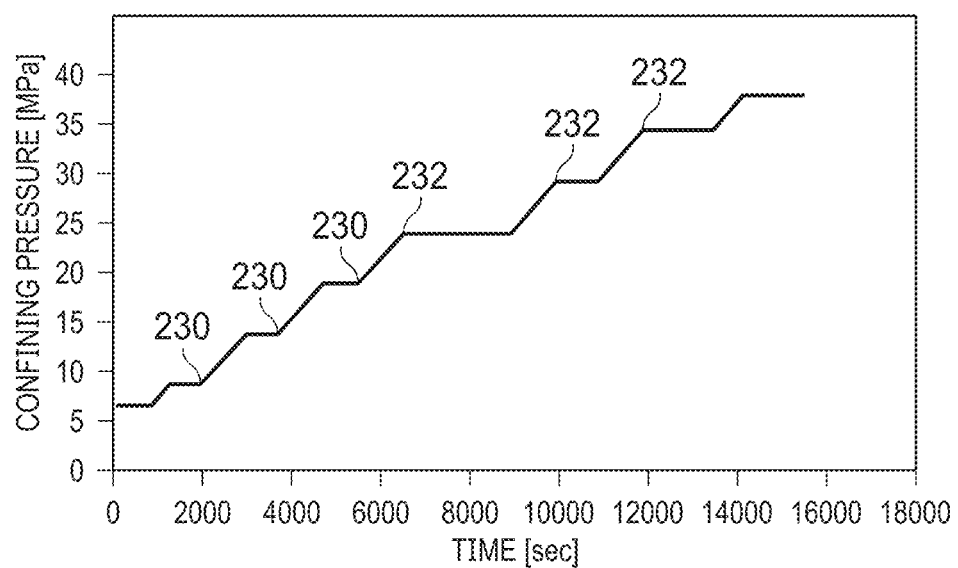
FIG. 13 is a graphical display of pressure applied as a function of time during pore volume compressibility (PVC) and Stress-Dependent Permeability (SDk) testing according to the present invention.

This can be accomplished by halting the PVC testing at pre-determined stress levels or stations 232 (FIG. 13) and performing permeability measurements at stress levels imposed by the confining pressure. The PVC loading cycle is then re-started until a new station is reached (FIG. 13). The sequence can be programmed and executed automatically in available triaxial testing apparatus capable of performing automatically, or manually by an operator. In both cases, it is required that after each permeability measurement, the pore pressure is exactly equalized between the upstream side and the downstream side of the plug before starting the PVC loading path again.

Other details about the PVC and SDk testing during step 132 are like those described previously for steps 114 and 116. It should be noted that the variation in pore volume and the permeability measured during step 132 are related to the total porosity and permeability of the entire plug system (matrix+fracture). These two components are discriminated, as will be described.

If the plug tested contains a natural fracture and not an induced one, then the two stress tests may be performed separately. For this, it is assumed that the fracture asperities of the natural fracture deform elastically within the laboratory stress range planned for the experiment. In any case, performing the two experiments together may save time even though it is more complex operationally.

Step 134: Split Plug Post-Test CT Scan and Property Measurement

Step 134 is a repetition for the split plug of the measurements performed in step 110 and 112 for the intact plug as described previously. The objectives are the same, but the post-test split (fractured) plug is being examined and its properties measured.

More in detail, CT analysis during step 134 allows comparison of the fracture geometry before and after the tests. This provides indications about the asperity shearing process. The CCA porosity measurement provides an indication of the plastic (non-recoverable) fracture porosity variation that may be compared with the porosity variation deducted from the pore fluid expulsion during the PVC tests as a quality control indicator.

Step 136: Definition of the Sensitivity of Fracture Porosity and Permeability to Stress During step 136, a final response relationship (FIG. 14) is determined for the sensitivity of the fracture porosity and permeability to variations in the laboratory stress field. Response curves resulting from performance for the sensitivity of the plug matrix porosity and permeability to stress have already obtained as a final product of step 104, as is described previously.

Figure 14:
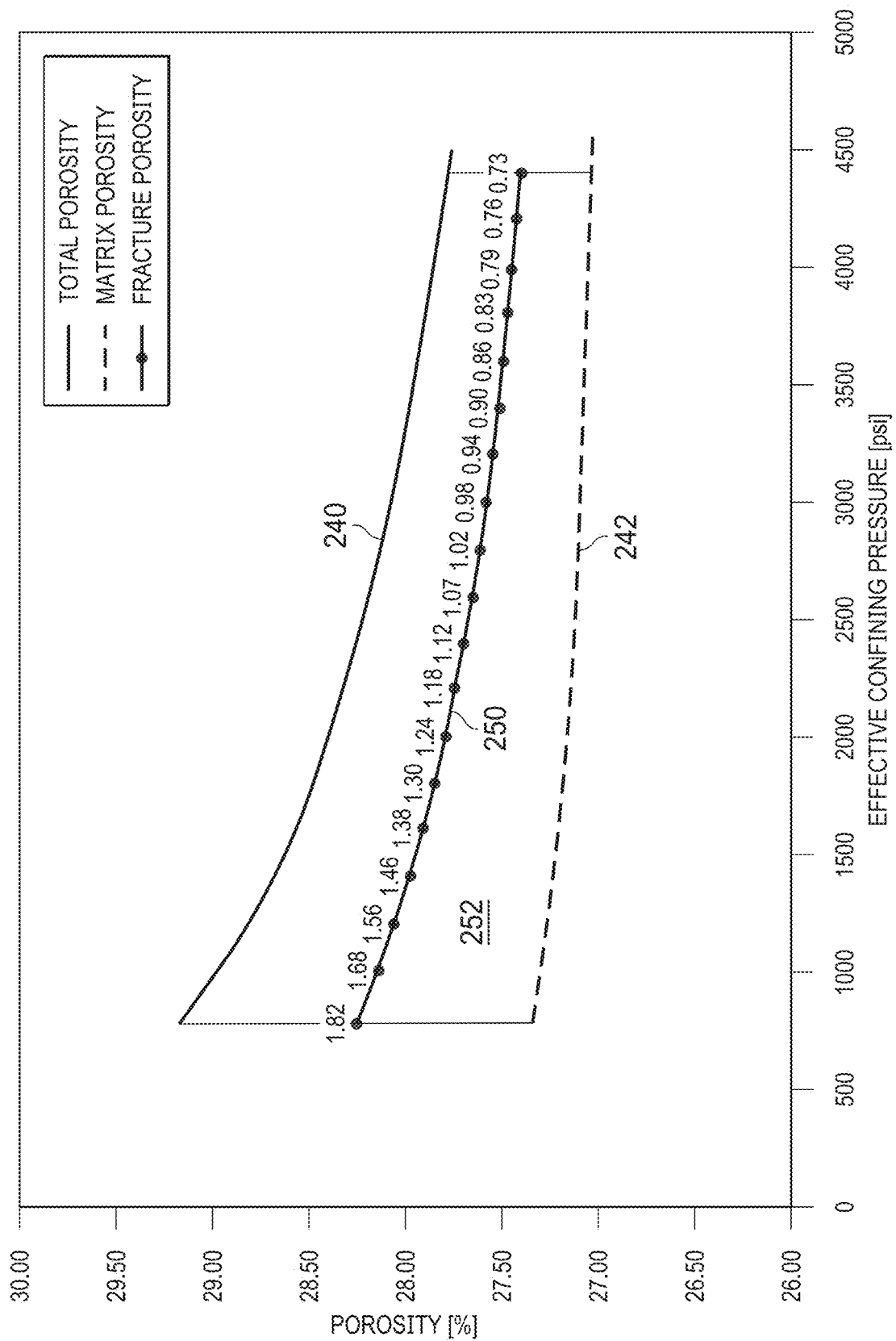
FIG. 14 is a display of results of fracture porosity variations as a function of pressure determined according to the present invention.

The total porosity is indicated at 240 in FIG. 14. The plug matrix porosity is indicated at 242. The results of the experiments conducted during step 114 provide porosity and permeability response curves to variations in the state of stress for the combined (matrix+fracture) system.

The final response curve for the fracture alone resulting from performance of step 136 as shown at 250 in FIG. 14. This relationship is obtained assuming that the superposition principle applies. Thus, the net response caused by the matrix pore space and the fracture pore space to stress variations is simply the sum of the individual responses that would have been caused by each type of pore space individually:

$$\Delta\varphi_{Tot}=\Delta\varphi_{Frac}+\Delta\varphi_{Matrix} \quad (2)$$

$$\Delta k_{Tot}=\Delta k_{Frac}+\Delta k_{Matrix} \quad (3)$$

Hence, at any given point along the graph for FIG. 14 representing the responses of the matrix 242 and the combined (matrix+fracture) system at 240, the porosity and permeability of the fracture may be graphically visualized at 252 as the space between plots of valves at 240 and 242. The magnitude at a specific state of stress is determined by subtracting the matrix porosity (FIG. 14) or permeability from the total porosity or permeability of the (matrix+fracture) system at the same state of stress.

To measure porosity ($\varphi$) and permeability (k) separately, first on an intact plug (matrix properties) and then on a Mode II axially fractured plug (matrix+fracture properties) with the same matrix. The results can then be used to extrapolate the required fracture properties of porosity ($\varphi$) and permeability (k).

The present invention allows measurement fracture properties of both porosity ($\varphi$) and permeability (k) from a single individual plug specimen in the course of experiments on servo-controlled triaxial apparatus. The fracture porosity and permeability measurements are obtained at stress conditions simulated based on the projected stress states expected during an entire life cycle of a reservoir.

The present invention provides for a direct measurement of fracture porosity and permeability in a laboratory as opposed to field measurements. Obtaining measurements in wells during production from wells in a reservoir by well testing requires interruption of well production which is undesirable. The present invention thus provides relevant time and cost savings, since reservoir testing during production is not required. The present invention can be applied to natural fractures included in cores and to laboratory created fractures.

The invention has been sufficiently described so that a person with average knowledge in the matter may reproduce and obtain the results mentioned in the invention herein. Nonetheless, should any skilled person in the subject matter of the present invention carry out modifications, or apply such modifications to a determined structure, or to performance of process, in a manner requiring the subject matter in the following claims; such modifications shall be covered within the scope of the present invention.

It should be noted and understood that there can be improvements and modifications made of the present invention described in detail in this document without departing from the spirit or scope of the invention as set forth in the accompanying claims.

What is claimed is:

1. A method of laboratory measurement of dynamic variations in petrophysical properties of a subsurface formation as a result of changes in stress applied to a core plug rock sample obtained from a location of interest in the subsurface formation, comprising the steps of:
  (a) performing computerized tomography on the core plug rock sample to determine a homogeneous density distribution in the core plug rock sample;
  (b) determining, responsive to determining the homogeneous density distribution in the rock sample and based on application of different levels of stress within a stress interval to the core plug rock sample, a matrix porosity/stress relationship for the core plug rock sample and a matrix permeability/stress relationship for the core plug rock sample, the matrix porosity/stress relationship corresponding to measured changes in porosity of the core rock plug sample for the different levels of stress applied to the core rock plug, and the matrix permeability/stress relationship corresponding to measured changes in permeability of the core rock plug sample for the different levels of stress applied to the core rock plug;
  (c) forming an axially extending shear fracture through the core plug rock sample to form a split core plug composed of fracture halves of the core plug rock sample;
  (d) moving the fracture halves of the split core plug axially with respect to each other to generate a moved split core plug that simulates displacement during in-situ fracture of formation rock of the subsurface formation;

(e) joining the fracture halves of the moved split core plug together to form a joined split plug comprising the fracture halves of the split core plug joined together and displaced axially with respect to each other; and (f) determining, based on application of different levels of stress within the stress interval to the joined split plug, a fracture porosity/stress relationship for the core plug rock sample and a fracture permeability/stress relationship of the core plug rock sample, the fracture porosity/stress relationship corresponding to measured changes in porosity of the joined split plug for the different levels of stress applied to the joined split plug, and the fracture permeability/stress relationship corresponding to measured changes in permeability of the joined split plug for the different levels of stress applied to the joined split plug.

2. The method of claim 1, wherein determining the matrix porosity/stress relationship for the core plug rock sample and the matrix permeability/stress relationship for the core plug rock sample comprises:

performing a pore volume compressibility test of the core plug rock sample to determine the matrix porosity/stress relationship for the core plug rock sample; and performing a stress-dependent permeability test of the core plug rock sample to determine the matrix permeability/stress relationship for the core plug rock sample.

3. The method of claim 2, further including the step of:
obtaining measurements of physical properties of the core plug rock sample before performing the pore compressibility test.

4. The method of claim 2, wherein the pore volume compressibility test is performed with the core rock sample under triaxial stress conditions.

5. The method of claim 2, wherein the pore volume compressibility test is performed with the core rock sample under hydrostatic stress conditions.

6. The method of claim 2, further including the step of:
obtaining measurements of physical properties of the core plug rock sample before performing the pore volume compressibility test.

7. The method of claim 1, wherein determining the fracture porosity/stress relationship for the core plug rock sample and the fracture permeability/stress relationship of the core plug rock sample comprises:

performing a pore volume compressibility test of the joined split plug to determine the fracture porosity/stress relationship for the core plug rock sample;

performing a stress-dependent permeability test of the joined split plug to determine the fracture permeability/stress relationship of the core plug rock sample.

8. The method of claim 7, wherein the pore volume compressibility test is performed under triaxial stress conditions.

9. The method of claim 7, wherein the pore volume compressibility test is performed under hydrostatic stress conditions.

\* \* \* \* \*